United States Patent [19]

Hefner, Jr.

[11] 4,419,299

[45] Dec. 6, 1983

[54] PHOSPHONOPOLYESTER OLIGOMERS

[75] Inventor: Robert E. Hefner, Jr., Lake Jackson, Tex.

[73] Assignee: The Dow Chemical Co., Midland, Mich.

[21] Appl. No.: 330,106

[22] Filed: Dec. 14, 1981

[51] Int. Cl.$^3$ .................................................. C07F 9/09
[52] U.S. Cl. ..................................... 260/929; 260/951; 525/42; 525/445; 528/72; 528/99; 528/167; 528/287
[58] Field of Search .................. 260/930, 951 US, 929

[56] References Cited

U.S. PATENT DOCUMENTS

| | | | |
|---|---|---|---|
| 2,560,350 | 7/1951 | Jelinek | 167/30 |
| 2,682,521 | 6/1954 | Coover | 260/47 |
| 2,682,522 | 6/1954 | Coover | 260/47 |
| 2,919,255 | 12/1959 | Hart | 260/23 |
| 2,926,145 | 2/1960 | McConnell et al. | 260/2 |
| 3,060,243 | 10/1962 | Ham | 260/613 |
| 3,578,731 | 5/1971 | Mange et al. | 260/929 |
| 4,148,765 | 4/1979 | Nelson | 260/22 CB |
| 4,233,432 | 11/1980 | Curtis | 528/298 |

FOREIGN PATENT DOCUMENTS 883754 12/1961 United Kingdom .

OTHER PUBLICATIONS

Encyclopedia of Polymer Science and Technology, 1967, p. 20, vol. 7, Published by John Wiley and Sons, Inc.
Polymer Science U.S.S.R. (Vysokomol. Soyed.) vol. 8, No. 6, pp. 1186-1192 (1966).
Kirk-Othmer, vol. 20, (1969) pp. 792-839.

*Primary Examiner*—Anton H. Sutto
*Attorney, Agent, or Firm*—J. G. Carter

[57] ABSTRACT

Phosphonopolyester oligomers are prepared from hydroxyalkylated 2,2',-bis(3-allylphenyl-4-hydroxy) alkanes and phosphonyl dihalides. The oligomers are useful in the preparation of polyester resins, epoxy resins, and polyurethanes.

3 Claims, No Drawings

PHOSPHONOPOLYESTER OLIGOMERS

BACKGROUND OF THE INVENTION

The present invention concerns phosphonopolyester oligomers and reaction products thereof.

Phosphorus-containing materials are well known as fire retardant agents in polymers such as polyester resins, polyurethane resins, epoxy resins and the like, particularly when employed in combination with a halogen such as chlorine or particularly bromine.

The present invention provides a method for incorporating phosphorus into the polymer chain of such resins and in certain instances the oligomers of the present invention contain chlorine or bromine in addition to phosphorus, in which instance a method for incorporating both phosphorus and a halogen into the polymer chain of the resins is provided.

SUMMARY OF THE INVENTION

The present invention pertains to an oligomer having recurring units represented by the following general formula

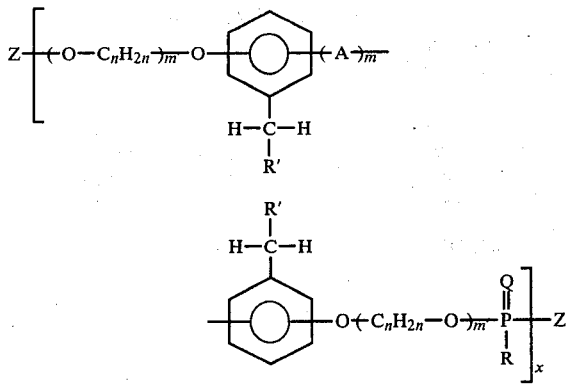

wherein each A is independently

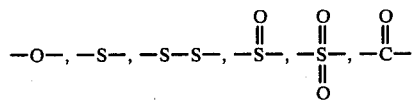

or a divalent hydrocarbon group having from 1 to about 8, preferably 1 to about 4, carbon atoms; each Q is independently oxygen or sulfur; each R is independently a hydrocarbon group having from about 1 to about 10, preferably from about 1 to about 6, carbon atoms; each R' is independently a —CH=CH$_2$ group or a —CXH—CXH$_2$ group, wherein X is chlorine or bromine; each Z is independently a terminal moiety; each m is independently zero or one; each m' independently has a value from 1 to about 5, preferably from about 1 to about 2; each n independently has a value of 2, 3 or 4; and x has an average value of from 1 to about 10, preferably from 1 to about 6.

The terminating moieties can be the same or different and are dependent on the ratio of the reactants employed to prepare the oligomer. When the phenolic hydroxyl-containing compound is in excess, most of the terminal moieties are that which provides terminal hydroxyl groups and when the phosphonyl halide is employed in excess, most of the terminal moieties are that which provides terminal phosphonate groups. Of course, it is recognized that the composition is actually a mixture of oligomers having various terminal moieties.

The present invention also pertains to polyurethanes, polyesters and epoxy resins prepared from the above oligomers.

DETAILED DESCRIPTION OF THE INVENTION

The oligomers of the present invention are prepared by reacting the desired dihydroxyl-containing compound with the desired phosphonyl dihalide or thiophosphonyl dihalide.

Suitable dihydroxyl-containing compounds which can be employed herein include those represented by the general formula

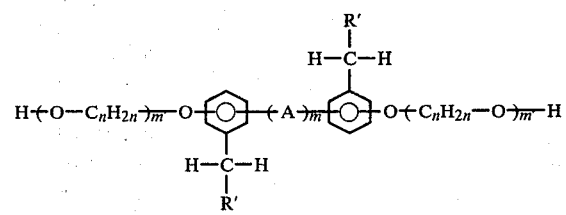

wherein each A, R', n, m and m' are as previously defined.

These compounds are readily prepared by alkoxylating with an appropriate alkylene oxide the allylated bisphenol compound or the brominated allylated bisphenol compound.

The bisallylated bisphenols employed herein can be prepared by reacting the appropriate bisphenol with an allyl halide in the presence of a suitable phase transfer catalyst such as DOWEX® MSA-1 ion exchange resin, benzyltrimethyl ammonium halides, tetramethylammonium halides, or tetraalkylphosphonium halides, and an aqueous solution of an alkali metal hydroxide such as NaOH at a temperature of from about 25° to about 100° C. for from about 2 to about 24 hours. Thereafter, the pH is adjusted from about 7 to about 3 and the product, a bisallylated bisphenol isomeric mixture, is recovered therefrom by separation of the oil and water phases. The resulting isomeric mixture is thermally isomerized at about 200° C. for 1 to 2 hours to provide C-bisallylated bisphenol. Mixtures of mono, di, and triallylated bisphenols are also operable.

Particularly suitable such compounds include, for example, dipropoxylated 2,2'-bis(3-allylphenyl-4-hydroxy)propane, diethoxylated 2,2'-bis(3-allylphenyl-4-hydroxy)propane, dipropoxylated bis(3-allylphenyl-4-hydroxy)methane, diethyoxylated or dipropoxylated bisallylated 4,4'-dihydroxybiphenyl or 4,4'-dihydroxydiphenyl oxide or 4,4'-thiodiphenol, and the like.

Suitable phosphonyl halides or thiophosphonyl halides which can be employed herein include those represented by the general formula

wherein each Q, R, and X is as previously defined.

Unsaturated polyester resins can be prepared by reacting the oligomers of the present invention with polycarboxylic acids, anhydrides, or mixtures thereof. The oligomers may be employed alone as the sole source of hydroxyl groups or they can preferably be employed in combination with polyhydroxyl-containing materials such as aliphatic glycols. Suitable such polycarboxylic acids or anhydrides thereof and polyhydroxyl-containing materials which can be employed to prepare unsaturated polyester resins as well as methods for such preparation and the crosslinking and/or curing thereof can be found in *KIRK OTHMER ENCYCLOPEDIA OF CHEMICAL TECHNOLOGY,* Vol. 20, pages 792-839, 1969, John Wiley & Sons, Inc. which is incorporated herein by reference.

Particularly suitable polyesters are prepared by a hydrolysis method wherein dicyclopentadiene or a dicyclopentadiene concentrate containing cyclopentadiene codimers and diolefin dimers is reacted with a $\alpha,\beta$-unsaturated dicarboxylic acid anhydride and water to provide a mixture consisting principally of dicyclopentadiene monomaleate and unreacted $\alpha,\beta$-unsaturated dicarboxylic acid and anhydride. Alternately, the dicyclopentadiene and a $\alpha,\beta$-unsaturated dicarboxylic acid may be reacted directly without water as a coreactant. The oligomer of the present invention plus a suitable glycol, polyol or mixture thereof is added and polyesterification is completed by removal of water at elevated temperatures. Suitable hydrolysis methods are more fully described in U.S. Pat. No. 4,148,765 and U.S. Pat. No. 4,233,432.

It is particularly desirable to perform the hydrolysis in a staged manner wherein the dicyclopentadiene or dicyclopentadiene concentrate and water are added in increments. This provides for additional control over reaction exotherms. This method is more fully described in the aforementioned U.S. Pat. No. 4,148,765.

Epoxy resins can be prepared from the oligomers of the present invention by reaction with an epihalohydrin in the presence of suitable acid catalysts such as boron trifluoride etherate, stannic chloride, and the like as described in *HANDBOOK FOR EPOXY RESINS,* by Lee and Neville, McGraw-Hill, 1967. The book also describes methods for curing epoxy resins such as with amines, polycarboxylic acids and anhydrides thereof and the like. The handbook by Lee and Neville is incorporated herein by reference.

Polyurethanes can be prepared from the oligomers of the present invention by reacting them with organic polyisocyanates in the presence of suitable catalysts. The oligomers can be employed alone or in combination with other hydroxyl-containing materials. Suitable hydroxyl-containing materials, polyisocyanates, and catalysts, as well as suitable methods for conducting the reaction, can be found in *POLYURETHANES: CHEMISTRY AND TECHNOLOGY II. TECHNOLOGY,* by Saunders and Frisch, Interscience, 1964 which is incorporated herein by reference.

The following examples are illustrative of the invention but are not to be construed as to limiting the scope thereof in any manner.

EXAMPLES 1-3

In a series of reactions, the bispropoxylate of 2,2'-bis(3-allylphenyl-4-hydroxy)propane, 84.92 grams (0.20 mole), was charged to a 3-necked round bottom reactor equipped with a thermometer-temperature controller assembly and heating mantle. A dry nitrogen inlet was fitted to the reactor and adjusted to maintain nitrogen flow over the surface of the reactants. Magnetic stirring was employed. A condenser and a side arm vented addition funnel containing phenylphosphonyl dichloride, 37.05 grams (0.19 mole), were added to complete the reactor. Heating commenced, and once the minimum reaction temperature, as specified in Table I, was achieved, the phenylphosphonyl dichloride was added dropwise over the specified time interval and temperature range. A post reaction was then completed for the specified time interval and temperature range. Finally, additional post reaction was performed under vacuum of about 80 to 10 mm for the specified time interval and temperature range. At the end of the vacuum post reaction, the phosphonopolyester oligomer product was recovered as a light amber colored solution which became an immobile gel at (25° C.) room temperature. The product was weighed and analyzed for average molecular weight by gel permeation chromatography. The results are reported in Table I.

COMPARATIVE EXPERIMENTS A-C

A series of comparative experiments were completed using the method of Examples 1-3, with the following changes:

C.E. A: 2,2'-bis(3-allylphenyl-4-hydroxy)-propane, 30.84 grams (0.10 mole), was substituted for the corresponding bispropoxylate of Examples 1-3. Phenylphosphonyl dichloride was correspondingly reduced to 18.52 grams (0.095 mole) to maintain the stoichiometric ratio of examples 1-3. The results are reported in Table I.

C.E. B: The bispropoxylate of 4,4'-isopropylidenediphenol, 68.80 grams (0.20 mole) was substituted for the 2,2'-bis(3-allylphenyl-4-hydroxy)propane of Examples 1-3. The results are reported in Table I.

C.E. C: 2,2'-bis(3-allylphenyl-4-hydroxy)propane, 63.69 grams (0.15 mole) was reacted with dichlorophenylphosphine, 25.51 grams (0.1425 mole). The results are reported in Table I.

TABLE I

| Example | Reaction Time (min.)<br>(a) phosphorus dihalide addition<br>(b) post reaction<br>(c) vacuum post reaction | | Reaction Temperature (°C.)<br>(a) initial-maximum<br>(b) minimum-maximum<br>(c) minimum-maximum | | Average Molecular Weight[1] | Conversion[3] (%) |
|---|---|---|---|---|---|---|
| 1 | (a) | 80 | (a) | 40-54 | 1282 | 82 |
|   | (b) | 119 | (b) | 74-102 |   |   |
|   | (c) | 995 | (c) | 69-100 |   |   |
| 2 | (a) | 30 | (a) | 40-50 | 2776 | 100 |
|   | (b) | 154 | (b) | 50-102 |   |   |
|   | (c) | 1040 | (c) | 90-105 |   |   |
| 3 | (a) | 30 | (a) | 39-60 | 2239 | 100 |
|   | (b) | 180 | (b) | 60-100 |   |   |
|   | (c) | 1080 | (c) | 75-108 |   |   |
| C.E. A | (a) | 30 | (a) | 38-63 | 253 | — |
|   | (b) | 120 | (b) | 68-110 |   |   |

TABLE I-continued

| Example | Reaction Time (min.)<br>(a) phosphorus dihalide addition<br>(b) post reaction<br>(c) vacuum post reaction | | Reaction Temperature (°C.)<br>(a) initial-maximum<br>(b) minimum-maximum<br>(c) minimum-maximum | | Average Molecular Weight[1] | Conversion[3] (%) |
|---|---|---|---|---|---|---|
|  | (c) | 45[2] | (c) | 101–110 |  |  |
| C.E. B | (a) | 30 | (a) | 45–60 | 985 | 83 |
|  | (b) | 120 | (b) | 64–102 |  |  |
|  | (c) | 960 | (c) | 99–107 |  |  |
| C.E. C | (a) | 30 | (a) | 50–72 | 255 | 60 |
|  | (b) | 180 | (b) | 62–106 |  |  |
|  | (c) | 60 | (c) | 100–106 |  |  |

[1]polystyrene standards
[2]reaction terminated - phenylphosphonyl dichloride distills overhead during the vacuum post reaction.
[3]based on weight of HCl lost.

EXAMPLE 4

The bispropoxylate of 2,2'-bis(3-allylphenyl-4-hydroxy)propane, 63.69 grams (0.15 mole), and phenylphosphonyl dichloride, 27.79 grams (0.1425 mole), were reacted using the method of examples 1–3 except that 150 grams of chloroform was used as a solvent for the reaction. Make-up chloroform was added as required to maintain a constant volume. All chloroform was allowed to distill out of the reactor during the vacuum post reaction. The following results were obtained:
Reaction time (min.)
  (a) phosphorus dihalide addition—4
  (b) post reaction—352
  (c) vacuum post reaction—925
Reaction temperature (°C.)
  (a) initial-maximum—50–54
  (b) minimum-maximum—52–116
  (c) minimum-maximum—100–120
Average Molecular Weight—1193

EXAMPLE 5

The bispropoxylate of 2,2'-bis(3-allylphenyl-4-hydroxy)-propane, 63.69 grams (0.15 mole), and phenylphosphonyl dichloride, 29.25 grams (0.15 mole), were reacted using the method of Examples 1–3. Exactly stoichiometric ratios of the aforementioned reactants are used in this example whereas less than stoichiometric phenylphosphonyl dichloride was used in Examples 1–4. The following results were obtained:
Reaction time (min.)
  (a) phosphorus dihalide addition—20
  (b) post reaction—130
  (c) vacuum post reaction—78
Reaction temperature (°C.)
  (a) initial-maximum—38–62
  (b) minimum-maximum—60–102
  (c) minimum-maximum—101–114
Average Molecular Weight—776
Conversion (%)—96

EXAMPLE 6

A phosphonopolyester oligomer product was synthesized using the method and stoichiometry of examples 1—3. The average molecular weight was 1136. This product was used as one of the components in the synthesis of a dicyclopentadiene modified unsaturated polyester alkyd, as follows:

Maleic anhydride, 98.06 grams (1.0 mole), was charged to a reactor and melted to a clear stirred solution maintained at 70° C. under a nitrogen atmosphere. Water, 9.46 grams (0.525 mole), was added followed by the addition of an increment of dicyclopentadiene concentrate, 20.05 grams, two minutes later. The dicyclopentadiene concentrate contained 83.94% dicyclopentadiene, 14.41% codimers and dimers, 1.11% light hydrocarbons, and 0.55% cyclopentadiene. Twenty minutes later, additional increments of water, 3.15 grams (0.175 mole), and dicyclopentadiene concentrate, 20.05 grams, were added. After 15 minutes additional dicyclopentadiene concentrate, 20.05 grams, was added. A final increment of dicyclopentadiene concentrate, 20.05 grams, was added 15 minutes later and the temperature controller was set at 110° C. This temperature was achieved 15 minutes later. Thirty minutes later, propylene glycol, 53.42 grams (0.702 mole) and the phosphonopolyester oligomer, 88.58 grams (0.078 mole) were added and the steam condenser was started, nitrogen sparging was increased, and the temperature controller was set at 160° C. This temperature was achieved 15 minutes later. After two hours of reaction at 160° C., the temperature controller was set at 205° C. This temperature was achieved 35 minutes later. Reaction continued for 2.0 hours at 205° C. during which time a total of 12 milliliters of water layer and 1.5 milliliters of organic material were removed through the steam condensor and into the Dean Stark trap-cold water condenser assembly. The reactor was cooled to 170° C. and 100 ppm of hydroquinone was added as an inhibitor. The polyester alkyd was recovered as a light amber solid with a final acid number of 45.9.

The polyester alkyd (57.0 percent) was dissolved in styrene (43.0 percent). The resulting formulation was used to determine Brookfield viscosity (25° C.), SPI gel and cure times plus maximum exotherm, and Barcol hardness. Circular, clear, unfilled castings of 0.5 cm. thickness and 3.5 cm. diameter were used in the evaluation of chemical resistance to water and toluene. These castings were prepared using a cure system of 1.0 percent methylethylketone peroxide and 0.3 percent VN-2 accelerator and 0.01 percent dimethylaniline, followed by 2.0 hours of post curing at 200° F. The following results were obtained:
Brookfield viscosity (cp)—1145
SPI Gel (84° C.)
  gel time—3.8 min.
  cure time—16.1 min.
  max. exotherm—99 min.
Chemical Resistance Testing
  (A) Water—7 days at 25° C.
    initial Barcol hardness—46
    final Barcol hardness—46
    weight gain (%)—0.24
    appearance—no change
  (B) Toluene—7 days at 25° C.

initial Barcol hardness—48.7
final Barcol hardness—49.0
weight gain (%)—0.22
appearance—no change

EXAMPLE 7

A propoxylate of 2,2'-bis(3-allylphenyl-4-hydroxy)-propane containing 1.075 propylene oxide units per aromatic hydroxyl group was prepared. Using the methods of Examples 1–3, 61.0 grams (0.1408 mole) of the propoxylate was reacted with 24.71 grams (0.1267 mole) of phenylphosphonyl dichloride using the following reaction conditions.

Reaction time (min.)
  (a) phosphorus dihalide addition—1
  (b) post reaction—85
  (c) vacuum post reaction—108.
Reaction temperature (°C.)
  (a) initial-maximum—40–41
  (b) minimum-maximum—41–100
  (c) minimum-maximum—100–100

The phosphonopolyester oligomer product had an average molecular weight of 1876. Full conversion of phenylphosphonyl dichloride to product was achieved.

EXAMPLE 8

The phosphonopolyester oligomer product of example 7 was used as one of the components in the synthesis of a dicyclopentadiene modified unsaturated polyester alkyd, as follows:

Maleic anhydride (196.12 grams, 2.0 moles) was charged to a reactor and melted to a clear stirred solution maintained at 70° C. under a nitrogen atmosphere. Water (18.92 grams, 1.05 mole) was added followed by the addition of an increment of dicyclopentadiene concentrate (39.79 grams, 0.30 mole) two minutes later. A maximum exotherm of 113° C. resulted. The dicyclopentadiene concentrate contained 86.05% dicyclopentadiene, 13.64% cyclopentadiene codimers and dimers, and 0.31% light hydrocarbons. Twenty minutes later, additional increments of water (6.31 grams, 0.35 mole) and dicyclopentadiene concentrate (39.79 grams, 0.30 mole) were added. After fifteen minutes, additional dicyclopentadiene concentrate (39.79 grams, 0.30 mole) was added. A final increment of dicyclopentadiene concentrate (39.79 grams, 0.30 mole) was added fifteen minutes later and the temperature controller was set at 110° C. This temperature was achieved six minutes later. Thirty minutes later, propylene glycol (116.28 grams, 1.528 moles) and the phosphonopolyester oligomer (60.0 grams, 0.032 mole) were added and the steam condenser was started, nitrogen sparging was increased to 4 liters per minute, and the temperature controller was set at 160° C. This temperature was achieved 19 minutes later. After two hours at the 160° C. reaction temperature, the temperature controller was set at 205° C. This temperature was achieved 16 minutes later. Reaction continued for 2.75 hours at 205° C. after which time a total of 49.0 milliliters of water layer and 2.5 milliliters of organic material had been removed through the steam condenser and into the Dean Stark trap-cold water condenser assembly. The reactor was cooled to 165° C. and 100 ppm of hydroquinone was added as an inhibitor. The polyester alkyd was recovered as a pale yellow solid with a final acid number of 29.7.

The polyester alkyd (171.0 grams) and styrene (129.0 grams) were mixed to form a 43.0% styrenated solution. The resulting solution was used to determine SPI gel characteristics, Brookfield viscosity (25° C.), and a clear, unfilled casting was made for heat distortion temperature, Barcol hardness, tensile and flexural strength, and oxygen index testing. Oxygen index values were determined by ASTM D2863-76. A cure system of 1.0% benzoyl peroxide and 0.01% dimethylaniline was used to cure the casting at room temperature followed by post curing for 2.0 hours at 93° C. (200° F.). The following results were obtained:

Brookfield viscosity at 25° C.—190.5 cp.
SPI Gel (84° C.)
  gel time—2.6 min.
  cure time—3.4 min.
  maximum exotherm—214° C.
Heat Distortion Temperature—181° F.
Average Barcol Hardness—41.5
Tensile Strength—4016 psi (282.3 kg/cm$^2$)
Elongation—0.99%
Flexural Strength—9773 psi (687 kg/cm$^2$)
Flexural Modulus—4.98×10$^{-5}$ psi (3.5×10$^{-6}$ kg/cm$^2$)
Oxygen Index—atmospheric

EXAMPLE 9

A portion of the polyester alkyd (253.0 grams) of example 8 was dissolved in 1200 milliliters of methylene chloride then chilled to −20° C. and held under a nitrogen atmosphere. Bromine (78.33 grams) was added over a 41 minute period followed by 60 minutes of post reaction at the −20° C. temperature. An inhibitor-stabilizer package consisting of 0.02% t-butyl catechol, 1.0% styrene, and 2.0% of the diglycidyl ether of a polyglycol (sold commercially as D.E.R. ® 736 epoxy resin) having an epoxy equivalent weight of 175-205 was added and the solution was allowed to warm to 25° C. The methylene chloride solvent was removed under reduced pressure and styrene (190.86 grams) was added to form a 43.0% styrenated solution. The physical and mechanical properties of this formulation were determined using the method of example 8. The following results were obtained:

Brookfield viscosity at 25° C.—482 cp.
SPI Gel (84° C.)
  gel time—3.15 min.
  cure time—4.45 min.
  maximum exotherm—145.5° C.
Heat Distortion Temperature—116° F.
Average Barcol Hardness—30.0
Tensile Strength—4626 psi (536.1 kg/cm$^2$)
Elongation—1.55%
Flexural Strength—11,264 psi (791.9 kg/cm$^2$)
Flexural Modulus—12.76×10$^{-5}$ psi (8.97×10$^{-6}$ kg/cm$^2$)
Oxygen Index—28.2

COMPARATIVE EXPERIMENT D

A comparative dicyclopentadiene modified unsaturated polyester was prepared as follows:

A hydrolysis step was completed in identical manner to Example 8, After 30 minutes at the 110° C. reaction temperature, propylene glycol (118.72 grams, 1.56 moles) was added to the reactor and the steam condenser was started, nitrogen sparging was increased to 4 liters per minute, and the temperature controller was set at 160° C. The 160° C. temperature was reached 16 minutes later. After 2 hours at 160° C., the temperature controller was set at 205° C. and this temperature was achieved 20 minutes later. After 2.3 hours a total of 41.5 milliliters of water layer and 11.0 milliliters of organic material were collected in the Dean Stark trap. The reactor was cooled to 164° C. and 100 ppm of hydroquinone was added. The polyester alkyd was recovered as a light yellow solid with a final acid number of 34.7.

A 43.0% styrene-57.0% alkyd solution was prepared and used to determine the following physical properties:

Brookfield viscosity at 25° C.—60.5 cp
SPI Gel (84° C.)
 gel time—3.4 min.
 cure time—4.8 min.
 maximum exotherm—195° C.
Heat Distortion Temperature—231° F.
Average Barcol Hardness—47.7
Tensile Strength—3113 psi (218.8 kg/cm$^2$)
Elongation—0.71%
Flexural Strength—9951 psi (699.6 kg/cm$^2$)
Flexural Modulus—5.36×10$^{-5}$ psi (3.77×10$^{-6}$ kg/cm$^2$)
Oxygen Index—atmospheric

EXAMPLE 10

A phosphonopolyester oligomer was prepared from the bispropoxylate of 2,2'-bis(3-allylphenyl-4-hydroxy)-propane and phenylphosphonyl dichloride using the methods and stoichiometry of Examples 1-3. The average molecular weight was 1193. A portion of the oligomer, 30.0 grams (0.0252 mole) was dissolved in 1,4-dioxane, 100 grams, containing diphenylmethane-4,4'-diisocyanate, 3.30 grams (0.0277 mole). The solution was maintained at reflux (102°-104° C.) for 2.0 hours. After removal of the solvent, a thermoplastic phosphonopolyesterurethane with high surface gloss, was recovered. The average molecular weight was 5199.

EXAMPLE 11

A phosphonopolyester oligomer was prepared fom the bispropoxylate of 2,2'-bis(3-allylphenyl-4-hydroxy)-propane and phenylphosphonyl dichloride using the methods and stoichiometry of Examples 1-3. The average molecular weight was 1282. A portion of the oligomer, 50.0 grams (0.0390 mole) and dipropylene glycol, 5.233 grams (0.0390 mole) were dissolved in 1,4-dioxane, 100 grams, containing diphenylmethane-4,4'-diisocyanate, 20.42 grams (0.0858 mole). The solution was maintained at reflux (106°-112° C.) for 2.0 hours. After removal of the solvent a thermoplastic phosphonopolyesterurethane with high surface gloss was recovered. The average molecular weight was 4581.

I claim:

1. An oligomer having recurring units represented by the following general formula

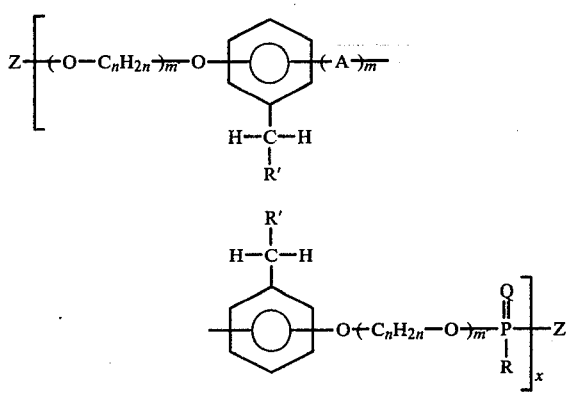

wherein each A is independently

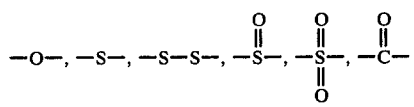

or a divlaent hydrocarbon group having from 1 to about 8 carbon atoms; each Q is independently oxygen or sulfur; each R is independently a hydrocarbon group having from about 1 to about 10 carbon atoms; each R' is independently a —CH=CH$_2$ group or a —CXH—CXH$_2$ group, wherein X is chlorine or bromine; each Z is independently a moiety such that the terminal groups are hydroxyl or phosphonate groups or combination thereof; each m is independently zero or one; each m' independently has a value from 1 to about 5; each n independently has a value of 2, 3 or 4; and x has an average value of from 1 to about 10.

2. An oligomer of claim 1 wherein each A is independently a divalent hydrocarbon group having from 1 to about 4 carbon atoms; Q is oxygen; each R is independently a hydrocarbon group having from about 1 to about 6 carbon atoms; each m has a value of 1, each m' independently has a value of from about 1 to about 2; each n has a value of 3; and x has an average value of from about 1 to about 10.

3. An oligomer of claim 2 wherein each A independently is a divalent hydrocarbon group having either 1 or 3 carbon atoms; each m' has a value of 1; and n has a value of 3.

* * * * *